(12) United States Patent
Peyman et al.

(10) Patent No.: US 8,121,663 B2
(45) Date of Patent: Feb. 21, 2012

(54) PHOTOACOUSTIC MEASUREMENT OF ANALYTE CONCENTRATION IN THE EYE

(76) Inventors: Gholam A. Peyman, Tucson, AZ (US); Shin Yoneya, Maebashi (JP)

( * ) Notice: Subject to any disclaimer, the term of this patent is extended or adjusted under 35 U.S.C. 154(b) by 985 days.

(21) Appl. No.: 11/870,935

(22) Filed: Oct. 11, 2007

(65) Prior Publication Data

US 2008/0033262 A1 Feb. 7, 2008

Related U.S. Application Data

(63) Continuation of application No. 11/323,232, filed on Dec. 30, 2005, now abandoned.

(60) Provisional application No. 60/727,078, filed on Oct. 14, 2005.

(51) Int. Cl.
*A61B 5/1455* (2006.01)

(52) U.S. Cl. ....................................... 600/319; 600/316

(58) Field of Classification Search ........... 600/309–360
See application file for complete search history.

(56) References Cited

U.S. PATENT DOCUMENTS

| | | | |
|---|---|---|---|
| 3,958,560 A | 5/1976 | March | |
| 3,963,019 A | 6/1976 | Quandt | |
| 4,556,293 A | 12/1985 | Burns et al. | |
| 5,560,356 A | 10/1996 | Peyman | |
| 5,710,630 A | 1/1998 | Essenpreis et al. | |
| 5,941,821 A | 8/1999 | Chou | |
| 6,070,093 A | 5/2000 | Oosta et al. | |
| 6,403,944 B1 | 6/2002 | MacKenzie et al. | |
| 6,490,470 B1 | 12/2002 | Kruger | |
| 6,609,015 B2 | 8/2003 | Lucassen et al. | |
| 6,725,073 B1 | 4/2004 | Motamedi et al. | |
| 6,846,288 B2 | 1/2005 | Nagar et al. | |
| 2003/0167002 A1* | 9/2003 | Nagar et al. | 600/437 |
| 2004/0138539 A1* | 7/2004 | Jay et al. | 600/322 |
| 2005/0190372 A1 | 9/2005 | Dogariu | |

OTHER PUBLICATIONS

Levitz et al., Determination of optical scattering properties of highly-scattering media in optical coherence tomography images, Optics Express, vol. 12. No. 2 Jan. 2004.
Charters, Advance OCT opens way for 3-D retinal images, Ophthalmology Times, Aug. 2005.
Larin et al., Noninvasive Blood Glucose Monitoring with Optical Coherence Tomography, Diabetes Care, vol. 25, No. 12, Dec. 2002, p. 2263-2267.
Larin et al., Specificity of noninvasive blood glucose sensing using optical coherence tomography technique: a polit study, Phy. Med. Biol., No. 28, p. 1371-1390, May 2003.

(Continued)

*Primary Examiner* — Eric Winakur
*Assistant Examiner* — Marjan Fardanesh
(74) *Attorney, Agent, or Firm* — Thompson Hine LLP

(57) ABSTRACT

In one aspect, the invention features a method and device for measuring blood concentration of a substance such as glucose in the aqueous humor by illuminating the aqueous humor with a light source at a frequency that is absorbed by the substance to the measured, and then sensing photoacoustically generated sound waves originated within the aqueous humor as a consequence of illumination by the light source. The blood concentration can be estimated from the amplitude of the sound waves received. The method may be combined with other optical techniques for glucose measurement and/or with optical or ultrasonic techniques for topographic mapping of eye structures.

14 Claims, 1 Drawing Sheet

OTHER PUBLICATIONS

Khallil, Spectroscopic and Clinical Aspects of Noninvasive Glucose Measurements, Clinical Chemistry, vol. 45, No. 2, 1999, p. 165-177.

Rabinovitch et al., Noninvasive glucose monitoring of the aqueous humor of the eye: Part 1, Measurement of very small optical rotations. Diabetes Care, vol. 5, Issue 3, 1982, p. 254-258.

Fercher et al., Optical coherence tomography—principles and applications, 2003 Re. Prog. Phys. 66, p. 239-303, Jan. 2003.

Bonner, Diagnostic Devices of the New Millennium, An Optometric Odyssey, Spisode VIII, 23rd Annual diagnostic Technology Report, Aug. 2000.

Zvyagin et al., Refractive index tomography of turbid media by bifocal optical coherence refractometry, Optics Express, vol. 11, No. 25, Dec. 2003.

Glenn Research Center, *The Eye: Window to the Body*, John Glenn Biomedical Engineering Consortium, May 2002.

\* cited by examiner

PHOTOACOUSTIC MEASUREMENT OF ANALYTE CONCENTRATION IN THE EYE

CROSS REFERENCE TO RELATED APPLICATIONS

This application is a continuation of U.S. application Ser. No. 11/323,232, filed Dec. 30, 2005 now abandoned which claims priority to provisional U.S. application Ser. No. 60/727,078, filed Oct. 14, 2005; the disclosures of which are hereby incorporated by reference herein in their entirety.

FIELD OF THE INVENTION

The invention relates to a non-invasive, in-vivo method and a system for the determination of the concentration of a substance in different areas of the eye.

BACKGROUND OF THE INVENTION

Many medical diagnostic techniques project radiant energy into the body of an animal for testing for the existence of a biomedical disorder or condition. For example, the integrity of the skeletal structure may be examined by passing X-rays through the body. The dense bony material substantially blocks the passage of the X-rays, permitting a doctor or other medical care provider to visually inspect for fractures or other defects in the skeletal structure.

To examine the soft tissue of the body, other techniques are available. These include, among others, CAT scans and magnetic resonance imaging. Both project radiant energy onto the body for obtaining information about the physical structure of the body.

Further, measurement of the level of certain chemicals or compositions within the body is a diagnostic test of particular interest. Radiant energy may be used in these applications as passage of the radiant energy through particular chemicals or compositions often alters the radiant energy in a manner that can be measured and analyzed. For example, the monitoring of the glucose level of the blood is of particular importance to diabetics.

One method of measuring the person's glucose involves projecting polarized radiation onto the body and measuring the optical rotation of the radiation that passes through the body. This optical rotation corresponds to the concentration of the glucose within the body. However, to be effective in measuring the concentration of a component the radiation must be passed through a relatively thin area of the body.

In another example, Larin et al. (Diabetes Care, Vol 25, No. 12, p. 2263-2267) describes a method of the noninvasive blood glucose measurement with optical coherence tomography. The glucose concentration was determined by the slope of the OCT signals. A calibration curve, however, is needed for the glucose concentration.

U.S. Pat. No. 6,403,944, the disclosure of which is incorporated herein by reference, uses a photoacoustic effect for glucose measurement. Pulses of light at a wavelength for which light is absorbed by glucose (e.g., 1000-1800 nm) are directed from a light guide into soft tissue of the person's body, such as a fingertip. The light pulses are typically focused to a relatively small focal region inside the body part and light from the light pulses is absorbed by glucose and converted to acoustic energy. The kinetic energy causes temperature and pressure of the absorbing tissue region to increase and generates acoustic waves, known as "photoacoustic waves", that radiate out from the absorbing tissue. An acoustic sensor in contact with the soft tissue senses the photoacoustic waves, and the intensity of those waves is used to assay the glucose.

U.S. Pat. No. 5,941,821, which is hereby incorporated herein by reference, describes another glucometer that uses a photoacoustic effect. This device illuminates the skin surface with modulating light at a carrier wavelength at which glucose absorbs light. Glucose in the blood and interstitial fluid near the tissue surface, absorbs the light and converts the absorbed energy to kinetic energy that heats the tissue. Temperature of the tissue increases and decreases cyclically in cadence with the modulation of the light. The alternate heating and cooling of the tissue results in periodic heating of air in contact with the surface of the illuminated region, which generates sound waves in the air. A microphone measures these sound waves which are used to determine a concentration of glucose.

A third example is described by U.S. Pat. No. 6,846,288, owned by Glucon, Inc., which is hereby incorporated herein in its entirety. There, a region of interest is illuminated with at least one pulse of radiation having a wavelength at which the radiation is absorbed, to generate a change in acoustic properties of the region. Then, ultrasound is transmitted so that it is incident on the region. Changes in the incident ultrasound are measured, to determine an absorption coefficient for the radiation, which can be converted to a concentration of glucose.

Unfortunately, these approaches all suffer from a number of drawbacks. Specifically, light is scattered by body tissue, and thus even in the '904 patent where light is focused to a region inside the body, the location and size of the absorbing tissue region are not accurately known. Furthermore, the generated photoacoustic effect in soft tissue, and thus measurements of the patient's glucose levels, are not necessarily the result only of glucose concentration in the blood. Characteristics of the absorbing tissue region, such as density of blood vessels therein, can affect concentration of glucose in the absorbing region and are often not accurately known. Furthermore, calibration must account for the nature of the body part and its size, skin color, skin condition, body fat and other factors that affect light absorption, transmission and heating of soft tissue. Measurements of blood glucose levels can therefore be affected by unknown variables that substantially compromise the reliability of those measurements.

The above techniques and disclosures discuss applications on the soft tissue of the body via the skin. Other techniques have projected radiant energy through the cornea and aqueous humor of the eye to measure glucose. The concentration of glucose and oxygen in the cornea and aqueous humor reflects the concentration generally throughout the body, and so such measurements are diagnostically useful. However, several problems are associated with these techniques.

For example, in Quandt U.S. Pat. No. 3,963,019, radiant energy is projected into the eye and reflected off the iris. The reflected radiation is detected, and the optical rotation caused by passage of the reflected radiation through the cornea and aqueous humor is determined. However, this method suffers from poor sensitivity, in part because it relies on reflecting the radiant energy off the iris.

Other attempts, as shown in March U.S. Pat. No. 3,958,560 and March U.S. Pat. No. 4,014,321, project the radiant energy at a shallow angle into the cornea on one side of the eye, through the aqueous humor, and out the cornea on the opposing side of the eye. Although this test is able to achieve high accuracy, it is difficult to administer because of the shallow angle at which the radiant energy must be passed through the eye.

U.S. Pat. No. 5,560,356 describes a system that uses an implanted reflective device in the anterior chamber or cornea of the eye. The incident polarized beam of radiation is projected into through the aqueous humor and/or cornea and is refracted or optically rotated in an amount that is proportional to the concentration of glucose or other substance present. The altered beam is reflected to a receiver by an implanted reflective device and processed to determine the glucose concentration.

All of these methods, however, measure glucose in only one area of the eye at any one time, and each relies upon optical methods for transmission and return of information. It would be advantages to measure concentration of glucose or another substance without these limitations.

SUMMARY OF THE INVENTION

In one aspect, the invention features a method and device for measuring blood concentration of a substance such as glucose in the aqueous humor by a method that avoids the drawbacks of the above-described approaches. Specifically, this involves illuminating the aqueous humor with a light source at a frequency that is absorbed by the substance to the measured, and then sensing photoacoustically generated sound waves originated within the aqueous humor as a consequence of illumination by the light source. The blood concentration can be estimated from the amplitude of the sound waves.

This method has the advantage that the radiant energy used to stimulate the photoacoustic response need not pass through soft tissue, but rather passes through a relatively clear and optically transmissive media. Furthermore, this method has the advantage that light need not be reflected or otherwise directed to a detector for the measurement to be accomplished, as the measurement is accomplished from acoustic, rather than electromagnetic, response signals.

Although it has been known to use a photoacoustic method to measure blood glucose in opaque tissue such as through the skin, use of this method in the aqueous humor is believed to be new, and has distinct advantages over these known applications for the reason that the aqueous humor is relatively transparent, and thus permits focused illumination over a larger range of tissue structure than could be achieved in opaque areas. At the same time, the glucose concentration within the aqueous humor is reflective of the body as a whole and thus the quality of the measurement is not compromised.

BRIEF DESCRIPTION OF THE DRAWINGS

The invention will be described with reference to the following drawings, in which.

DETAILED DESCRIPTION OF THE INVENTION

In one embodiment of the inventive system, the glucose concentration is measured in the eye, by a photoacoustic assay such as that described in U.S. Pat. No. 6,846,288 (e.g. at Col. 13, line 62 to Col. 18, line 49) or in U.S. Pat. No. 6,403,944 each of which is incorporated by reference in their entirety.

Figure 1:
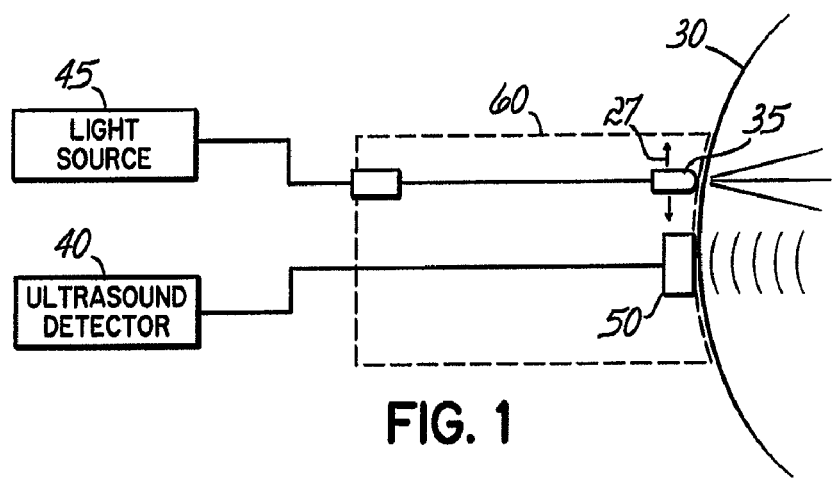
FIG. 1 illustrates a first embodiment of the invention for measuring photoacoustic signals developed within the eye in response to illuminating light.

As shown in FIG. 1, the probe module 60 includes an objective lens structure 35, which is coupled to a light source 45 via a fiber optic connection or other light transmitter. Light source 45 provides light at a wavelength which is preferentially absorbed by glucose. Alternatively, the light source may be incorporated into the probe module 60.

The light source 45 may be a laser, laser diode or superluminescent diode (SLD), as appropriate for generating the desired light wavelength and intensity. The light may be delivered as pulses or as modulated radiation.

The probe module 60 further contains an ultrasound transducer 50 to detect the photoacoustic waves that are generated as a result of the absorption of energy from the light emitted by the objective lens structure 35. The ultrasound transducer 50 is in contact with the eye 30 or an eyelid drawn over the eye. As light is delivered as pulses or as modulated radiation (as elaborated in the above-referenced U.S. Pat. Nos. 6,846, 288 and 6,403,944), pulses or modulating acoustic signals are generated and returned to the ultrasound transducer 50 in probe module 60. As noted, it is expected that substantially superior results, in repeatability and ease of calibration, will be achieved in the eye than are achieved in soft tissue as proposed by the '288 and '944 patents.

It will be appreciated that localization of the source of photoacoustic signals may be achieved in various manners. First, localization may be accomplished by directing the beam from objective lens structure 35 in specific directions, by moving that structure with micromechanical actuators as shown diagrammatically at 27 in FIG. 1, thus targeting a particular line of points in the eye. Furthermore, by suitable optics included in objective lens structure 35, the focal point of the emitted light may be moved within the eye to a desired point, such as a point along the retina vasculature, to selectively generate acoustic signals at that desired point. Because the eye is optically transmissive relative to soft tissue, beam focusing and beam directing are likely to be more accurately performed in the eye, than is the case is soft tissue elsewhere in the body.

To further assist in directionally capturing the photoacoustic signals generated within the eye, a directional transducer array may be used as transducer 50, to control the directionality of reception of ultrasonic energy, thus further localizing upon a desired source of thermoacoustic signals. Thus, by targeting the focal point of the illuminating light, and also directionally targeting the reception of ultrasonic signals by the transducer array, thermoacoustic signals from a particular location, such as along the retina, may be specifically targeted.

Mapping of patient eye structures is useful for analysis of macular edema, macular holes, glaucoma, various retinal diseases, neuroophthalmology, the anterior segment, and normal eye conditions. For such applications, it will be appreciated that the ultrasound transducer 50 may transmit and receive ultrasound waves; when transducer 50 transmits waves, reflected ultrasound waves may be used for imaging of eye structures, as is a known use of ultrasound for imaging. Eye structures localized with ultrasound may then be targeted by the optical system and transducer 50 for photoacoustic analysis. The combined use of sensors for ultrasound imaging and thermoacoustic reception is explained further in U.S. Pat. No. 6,490,470, which is hereby incorporated herein by reference in its entirety.

It will also be appreciated that the apparatus shown in FIG. 1 may be adapted to analyze glucose with reflected or transmitted ultrasound, i.e., ultrasound that passes through an irradiated area in the eye may be captured and its properties analyzed to determine glucose concentration, as discussed in U.S. Pat. No. 6,846,288. For such an application, an ultrasonically reflective structure may be utilized to reflect ultrasound transmitted into the eye so that the reflected ultrasound may be analyzed. The skull may be utilized for this purpose, or another reflector may be temporarily positioned within the eye socket for this purpose. Alternatively, an ultrasound emitter may be placed adjacent to the eye within the eye socket to generate ultrasound that may be received by a directionally-oriented receiver after passing through an area subject to illumination by light source 45.

Figure 2:
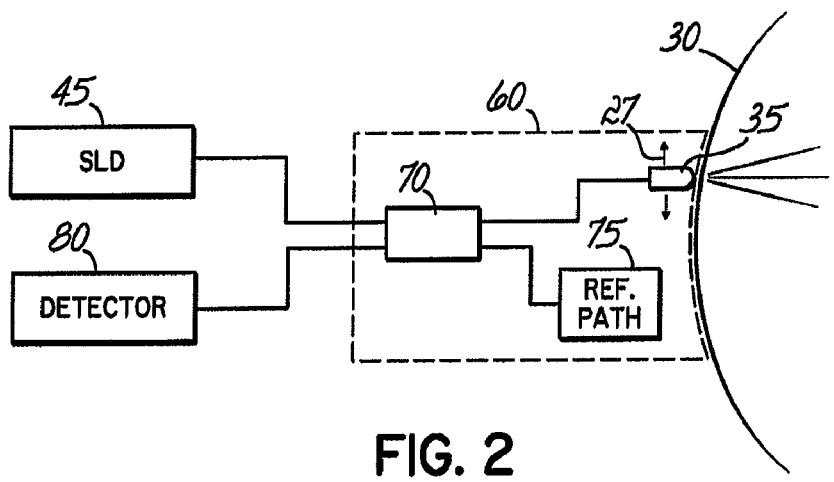
FIG. 2 illustrates an interferometry method for detecting glucose concentration in the eye.

In alternative embodiments of the invention, glucose concentrations within the eye may be measured in conjunction with a reflection interferometry method, such as a short coherence reflection interferometry method as generally described (for soft tissue) in U.S. Pat. No. 5,710,630 (Col. 10, line 20 to Col. 14, line 27). In this system, as shown in FIG. 2, the probe contains a superluminescent diode (SLD) light source 45 that transmits a wavelength of, e.g., 1300 nm, delivered to the imaging site through optical fiber and a coupler 70, into the eye 30. Light is also coupled from coupler 70 to a reference path 75, from which it is reflected to create interferometry with the reflections from the eye 30 at a photodetector 80. Movement of the objective lens 35 within the probe 60 as shown at 27 permits illumination of specific eye features. The characteristics thereof may then be detected from the changing interferometry between the reflected light received from lens 35 and reference path 75, as described in U.S. Pat. No. 5,710,630. By using a low-coherence-length light source 45 and measuring the interference between light backscattered from a tissue and from a mirror in the reference path 75, the distance and magnitude of optical scattering within the tissue is measured.

Figure 3:
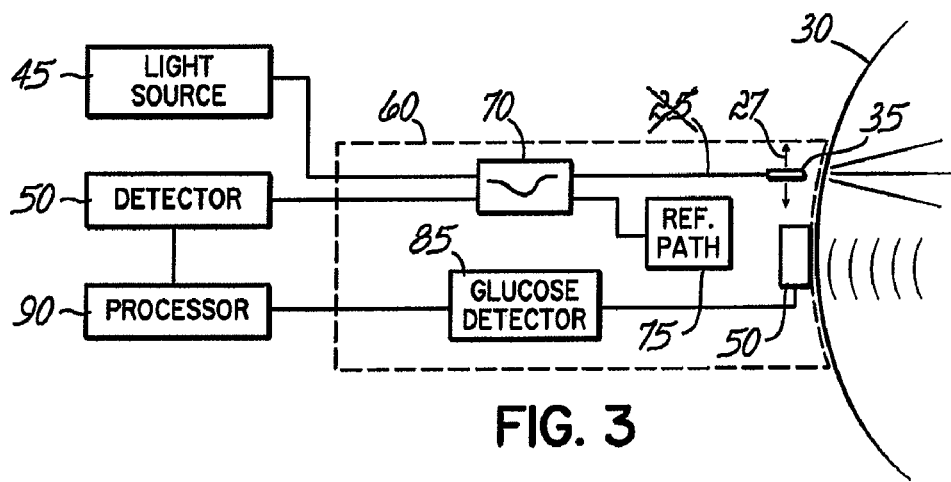
FIG. 3 illustrates a combined interferometry and photoacoustic system for detecting glucose concentrations at particular locations in the eye.

In a combined photoacoustic and interferometric system as illustrated in FIG. 3, the optical interferometry section generates light waves that reflect off the internal microstructure and also cause localized photoacoustic signal generation. Interferomatic techniques extract the reflected optical signals from the infrared light and the output, measured by an interferometer, is processed to produce glucose measurements as well as potentially cross sectional or 3-dimensional images of the target site.

In this combined embodiment, probe module 60 also includes an ultrasound transducer 50 and glucose detector system 85 of the kind discussed with reference to FIG. 1. A processor 90 attached to interferometry detector 50 and to glucose detector 85 combines the resulting signals from each (FIG. 3). Scanning the light beam across the tissue produces a cross-sectional image by the signal processor 90, while processor 90 records the axial reflectance profiles at each transverse position. Processor 90 also records glucose measurements at each location generated by inteferometric methods and from photoacoustic data generated in response to light illumination. The result is a multi-dimensional representation of the optical backscattering of the tissue's cross-section, which displays as a gray-scale or false-color image, and a superimposable measure of glucose.

While various embodiments have been chosen to illustrate the invention, it will be understood by those skilled in the art that various modifications can be made without departing from the spirit and scope of the invention as defined in the following claims.

What is claimed is:

1. A method of measuring the blood concentration of a substance in vivo, the method comprising
   illuminating the aqueous or vitreous humor or retinal fluid with a light source at a frequency that is absorbed by the substance to be measured,
   sensing only photoacoustically generated pulses or modulating acoustic signals originated within the aqueous or vitreous humor or retinal fluid as a consequence of illumination by the light source, without light being reflected or otherwise directed to a detector,
   estimating blood concentration of the substance from an amplitude of received pulses or modulating acoustic signals, and
   displaying the estimated blood concentration.

2. The method of claim 1 wherein the substance is blood glucose.

3. The method of claim 1 wherein the light source is a laser.

4. The method of claim 1 wherein the light source is a superluminescent diode.

5. An in vivo photoacoustic method of measuring the blood concentration of a substance, the method comprising
   illuminating a retinal surface with a light source at a frequency that is absorbed by the substance to be measured,
   sensing only photoacoustically generated pulses or modulating acoustic signals originated within the eye as a consequence of illumination by the light source, without light being reflected or otherwise directed to a detector,
   estimating blood concentration of the substance from an amplitude of received pulses or modulating acoustic signals only, and
   displaying the estimated blood concentration of the substance, the method photoacoustically measuring in vivo the blood concentration of the substance.

6. The method of claim 1 wherein the illuminating with the light source comprises delivering pulsed light is delivered as pulses.

7. The method of claim 1 wherein the illuminating with the light source comprises delivering is delivered as modulated radiation.

8. The method of claim 1 wherein the received sensed acoustic signal is ultrasound.

9. The method of claim 5 wherein the light source is a superluminescent diode.

10. The method of claim 5 wherein the substance is blood glucose.

11. The method of claim 5 wherein the light source is a laser.

12. The method of claim 5 wherein the illuminating with the light source comprises delivering pulsed light is delivered as pulses.

13. The method of claim 5 wherein the illuminating with the light source comprises delivering is delivered as modulated radiation.

14. The method of claim 5 wherein the sensed received acoustic signal is ultrasound.

* * * * *